United States Patent [19]

Makar

[11] Patent Number: 5,733,447
[45] Date of Patent: Mar. 31, 1998

[54] BUBBLE HUMIDIFIER INCLUDING PERMANENT MAGNETS FOR REDUCING THE GROWTH OF ALGAE THEREIN

[76] Inventor: Marko Makar, RR 1, Site 4, Box 18, Sparwood, B.C., Canada, V0B 2G0

[21] Appl. No.: 620,895

[22] Filed: Mar. 22, 1996

[51] Int. Cl.$^6$ ............................................. C02F 1/48
[52] U.S. Cl. .................... 210/220; 210/222; 261/121.1; 261/DIG. 46
[58] Field of Search ........................... 210/220, 222, 210/223, 695; 261/124, DIG. 46, 121.1; 128/200.11, 200.13, 203.16

[56] References Cited

U.S. PATENT DOCUMENTS

| | | | |
|---|---|---|---|
| 2,902,269 | 9/1959 | Eichelman | 261/124 |
| 4,013,742 | 3/1977 | Lang | 128/200.11 |
| 4,020,590 | 5/1977 | Davis . | |
| 4,065,386 | 12/1977 | Rigby | 210/695 |
| 4,157,963 | 6/1979 | Jessop et al. | 210/222 |
| 5,024,759 | 6/1991 | McGrath et al. . | |
| 5,190,648 | 3/1993 | Ramsauer | 210/220 |
| 5,227,683 | 7/1993 | Clair . | |
| 5,269,915 | 12/1993 | Clair . | |
| 5,269,916 | 12/1993 | Clair . | |
| 5,366,623 | 11/1994 | Clair . | |
| 5,460,718 | 10/1995 | Weck et al. | 210/205 |

FOREIGN PATENT DOCUMENTS

| | | | |
|---|---|---|---|
| 322544 | 7/1989 | European Pat. Off. | 210/695 |
| 2158059 | 11/1985 | United Kingdom | 210/222 |

*Primary Examiner*—Matthew O. Savage
*Attorney, Agent, or Firm*—Kolisch Hartwell Dickinson McCormack & Heuser

[57] ABSTRACT

A container for water. The container has walls and a base and a magnet located adjacent the base of the container. The magnet is positioned to be below the level of water in the container when water is present in the container. The invention find particular application in a bubble humidifier to humidify gas bubbled through water contained in the bubble humidifier prior to the gas passing to a patient.

3 Claims, 3 Drawing Sheets

BUBBLE HUMIDIFIER INCLUDING PERMANENT MAGNETS FOR REDUCING THE GROWTH OF ALGAE THEREIN

FIELD OF THE INVENTION

This invention relates to a container for water and, in a preferred embodiment, to a bubble humidifier to humidify gas bubbled through it.

BACKGROUND OF THE INVENTION

It seems clear that the exposing of water to a magnetic field has beneficial effects on the water. There is no clear scientific explanation of the phenomenon but a substantial number of patents exist in the field. Apart from the obvious advantages of removing magnetic impurities contained in the water, for example as a suspension, other beneficial advantages, notably inhibiting growth of algae are obtained.

The prior art systems of applying magnetic fields have been fairly elaborate. Patents known to applicant include U.S. Pat. No. 5,366,623 to Clair;

U.S. Pat. No. 5,227,683 to Clair;

U.S. Pat. No. 5,269,915 to Clair;

U.S. Pat. No. 5,269,916 to Clair;

U.S. Pat. No. 4,020,590 to Davis; and

U.S. Pat. No. 5,024,759 to McGrath

In general the prior art extends to quite complicated equipment. For example the work by Clair is concerned with arrangements that produce force lines or flux lines in a particular direction. Davis treats seeds by magnet to affect both the rate of germination and the rate of plant growth from the seed.

McGrath requires a particular disposition of a plurality of magnets mounted in a frame member.

It is known to feed oxygen to a patient to facilitate breathing. The oxygen is bubbled through water to humidify it. The equipment is normally referred to as a bubble humidifier. It is an apparatus having an inlet for oxygen in its top. A pipe extends from the inlet into a water container, to below the level of water in the container. There is an outlet in the top so that oxygen that has bubbled through the water in the container passes from the outlet to the patient.

The growth of algae in these bubble humidifiers is particularly acute, and, in a preferred aspect, the present invention provides a bubble humidifier with a reduced tendency to algae growth.

Accordingly, in a first aspect the invention is a container for water, the container having walls and a base and having a magnet located on the outside of the container, adjacent to the base of the container.

The magnet may be attached to the base of the container, preferably in a recess formed in the base. A plurality of magnets may be used. The magnet may have its north pole against the container or its south pole against the container or both the south and north poles against the container.

The magnet may be a bar magnet, or be disk shaped. The magnet may be a ferrite ceramic magnet or a ferrite bonded magnet.

In a preferred aspect the invention is a bubble humidifier to humidify a gas bubbled through said bubble humidifier prior to the gas passing to a patient, said bubble humidifier comprising:

a main body to contain water and having a base and walls;

a lid for the main body;

a gas inlet in the lid to attach to a source of gas;

a gas pipe extending from the gas inlet to adjacent the base of the container;

a gas outlet in the lid whereby gas bubbled through water in the container passes to the patient; and a magnet adjacent the main body to subject the water to a magnetic field to reduce algae growth in the water in the container.

In this aspect of the invention the magnet again may be housed in a recess in the wall or in the base of the water container. The recess in the wall is adjacent the base so as to be below the water level. The magnet may also be placed around the gas pipe. Typically these pipes increase in diameter adjacent the base, where there is a diffusion member. The magnet is prevented from slipping off the pipe by this increased diameter.

DESCRIPTION OF THE PREFERRED EMBODIMENTS

Figure 1:
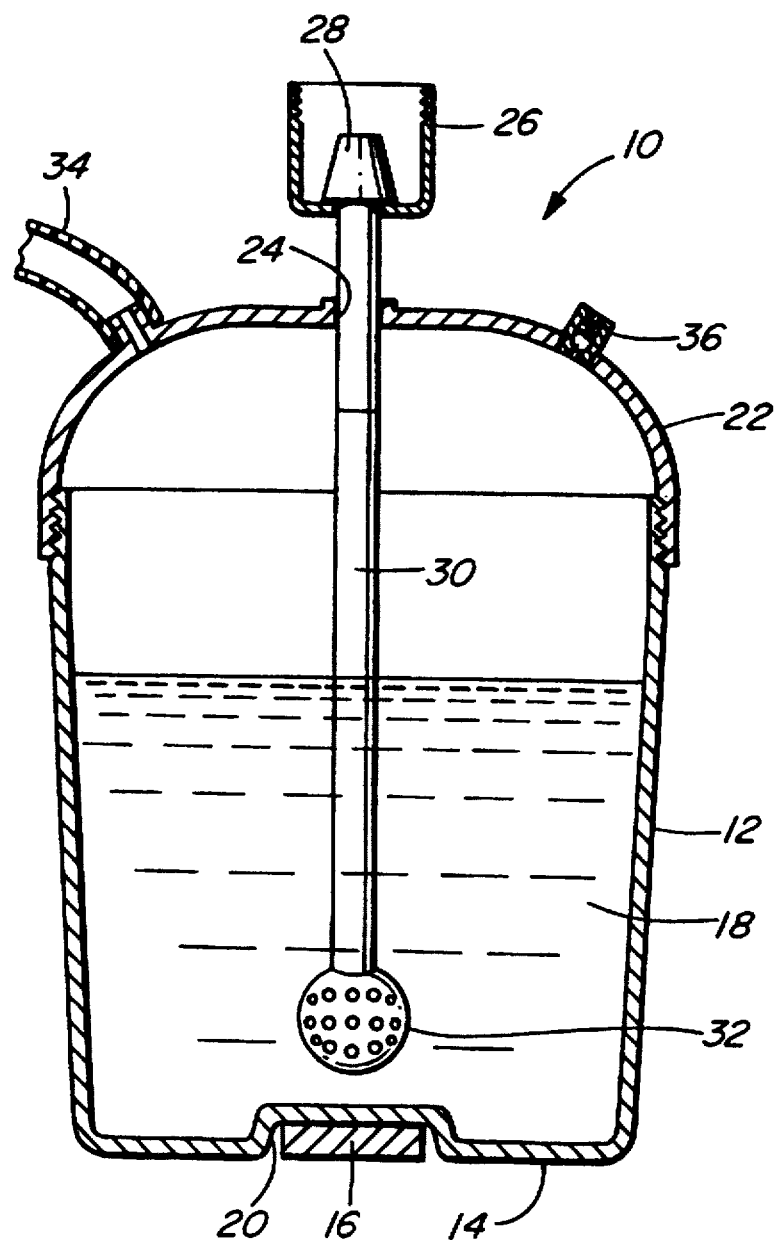
FIG. 1 is section through a bubbled humidifier according to the present invention.

Broadly stated FIG. 1 shows a container 10 for water. The container 10 has walls 12 and a base 14. There is magnet 16 located on the outside of the container 10. In FIG. 1 the magnet 16 is attached to the base 14 of the container 10. Magnet 16 is located in recess 20.

Figure 2:
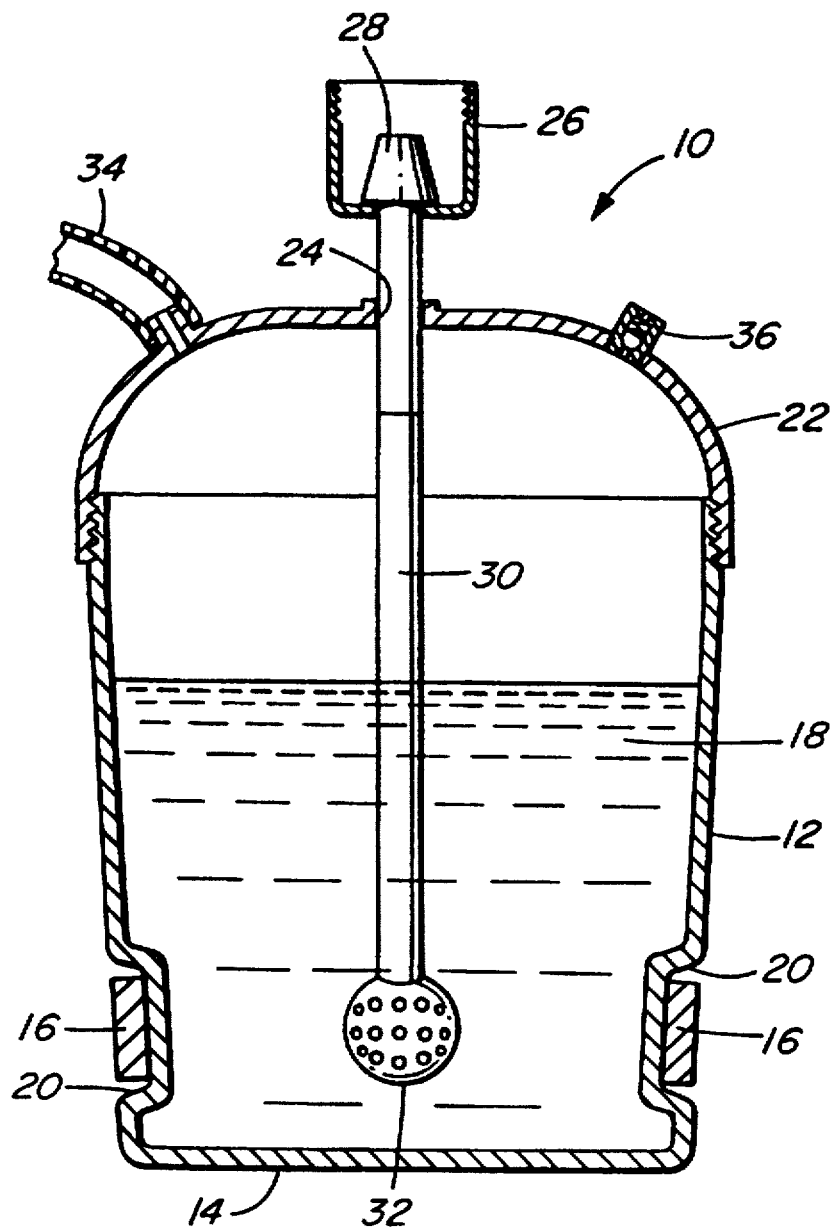
FIG. 2 is a detail of a variation of the embodiment of FIG. 1.

FIG. 2 illustrates the provision of recesses 20 to receive a pair of magnets 16. FIG. 2 illustrates the use of a plurality of magnets 16 on the outside of the container 10, in recesses 20.

Figure 3:
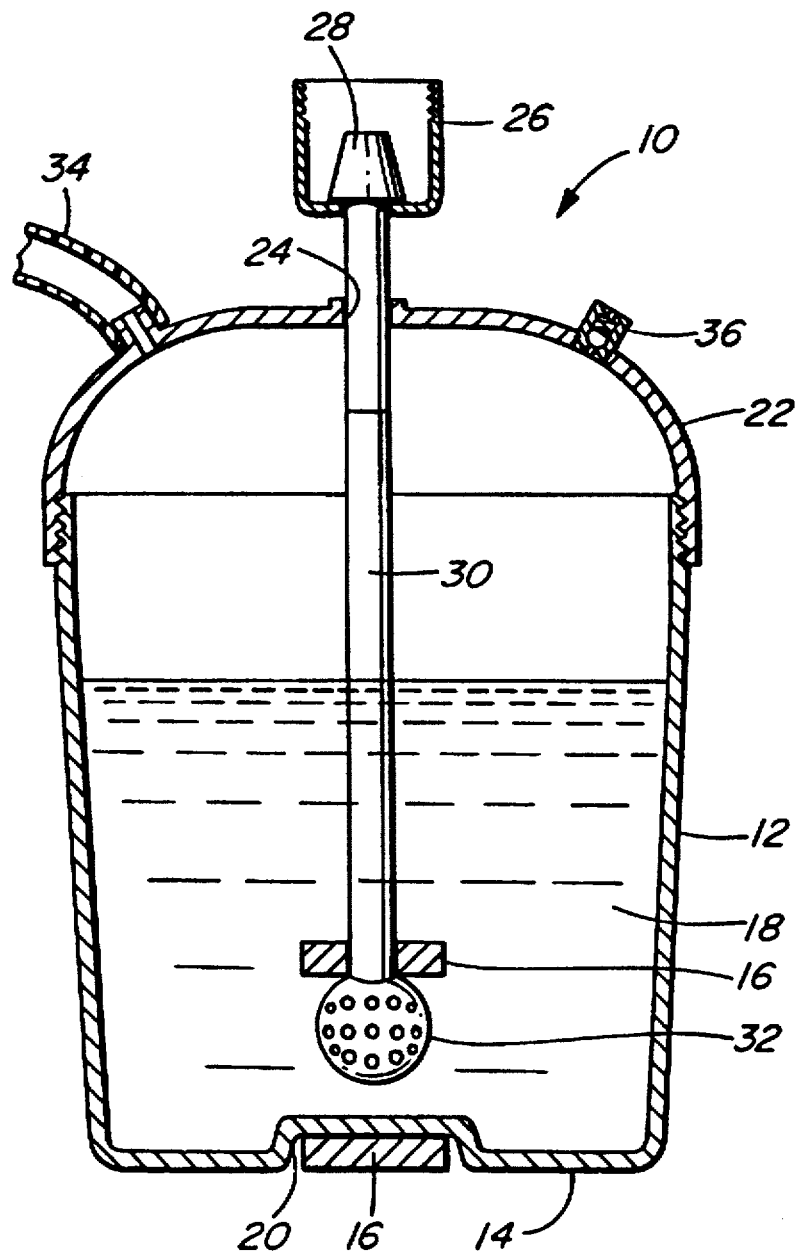
FIG. 3 is a view of a further variation of the embodiment of FIG. 1.

FIG. 3 shows two magnets 16, one in a recess 20 and one within the container 10.

In all cases the magnets 16 are at or adjacent the base 14 of the container 10 and below the level of the water 18 in the container.

More specifically, in FIG. 1 the container 10 is a bubble humidifier that humidifies a gas, usually oxygen, blown through the bubble humidifier prior to the gas passing to a patient. The bubble humidifier comprises container 10 to contain water 18. The container 10 has a base 14 and walls 12. There is a lid 22 for the container 10 that is threaded on to the container 10. A gas inlet 24 in the lid 22 attaches to a source of gas (not shown) by means of nut 26. A pipe (not shown) from the gas source is a close fit over a tapered end 28 of inlet 24. The pipe is provided with a threaded member that engages the nut 26, provided on the inlet 24, to provide a gas tight connection.

Pipe 30 extends from the gas inlet 24 to adjacent the base 14 of the container 10. The pipe 30 terminates in openings or jets 32 through which the gas bubbles. Water will typically be up to a level about half the height of the container 10.

There is a gas outlet 34 in the lid 22 whereby gas bubbled through the water passes to the patient.

According to the invention there is magnet 16 adjacent the base 14. The magnet 16 is attached to the exterior of the container 10. Typically the container 10 is of a plastic material.

The bubble humidifier is, as is standard in the art, provided with a pressure relief valve 36.

The magnet 16 is preferably mounted within the recess 20 in the base 14 of the bubble humidifier as shown in FIG. 1. The magnet 16 may be formed as an annulus and located on the pipe 30 as shown in FIG. 3. FIG. 2 shows the use of recesses 20 in the walls 12, adjacent base 14, so as to be below the level of any water 18 in the container 10 when the container is in use.

FIG. 3 shows two magnets 16 spaced from each other. This creates a magnetic field between the magnets 16. This may be suitable with weaker magnets, for example, bonded ferrite magnets.

A number of variations are possible. The drawings illustrate a cylindrical magnet 16. However the magnet may be a bar magnet. A ceramic magnet may be used as well as a conventional iron magnet or ferrite magnet.

Although the present invention has been described in some detail by way of example for purposes of clarity and understanding, it will be apparent that certain changes and modifications may be practised within the scope of the appended claims.

I claim:

1. A bubble humidifier to humidify a gas bubbled through said bubble humidifier prior to the gas passing to a patient, said bubble humidifier comprising:

a main body having a base, a peripheral side wall joined to said base and defining an open top end, wherein said base and said peripheral wall together define an interior chamber adapted to contain water therein; and a lid for closing the open top end of the main body;

a gas inlet in the lid to attach to a source of gas;

a gas pipe within said interior chamber and extending from the gas inlet to a location adjacent the base of the main body, said gas pipe defining an open end adjacent said base for discharging gas into said water;

a gas outlet in the lid whereby gas bubbled through the water in the container passes to the patient;

a recess in the base of the main body;

a permanant magnet disposed in the recess in the base of the main body to subject the water to a non-alternating magnetic field to reduce algae growth in the main body.

2. A bubble humidifier to humidify a gas bubbled through said bubble humidifier prior to the gas passing to a patient, said bubble humidifier comprising:

a main body having a base, a peripheral side wall joined to said base and defining an open top end, wherein said base and said peripheral wall together define an interior chamber adapted to contain water therein; and a lid for closing the open top end of the main body;

a gas inlet in the lid to attach to a source of gas;

a gas pipe within said interior chamber and extending from the gas inlet to a location adjacent the base of the main body, said gas pipe defining an open end adjacent said base for discharging gas into said water;

a gas outlet in the lid whereby gas bubbled through the water in the container passes to the patient;

a recess in the peripheral side wall of the main body;

a permanent magnet disposed in the recess in the peripheral side wall of the main body to subject the water to a non-alternating magnetic field to reduce algae growth in the main body.

3. A bubble humidifier to humidify a gas bubbled through said bubble humidifier prior to the gas passing to a patient, said bubble humidifier comprising:

a main body having a base, a peripheral side wall joined to said base and defining an open top end, wherein said base and said peripheral wall together define an interior chamber adapted to contain water therein; and a lid for closing the open top end of the main body;

a gas inlet in the lid to attach to a source of gas;

a gas pipe within said interior chamber and extending from the gas inlet to a location adjacent the base of the main body, said gas pipe defining an open end adjacent said base for discharging gas into said water;

a gas outlet in the lid whereby gas bubbled through the water in the container passes to the patient;

an annular permanent magnet surrounding the gas pipe and positioned between said gas inlet and the open end of said gas pipe to subject the water to a non-alternating magnetic field to reduce algae growth in the main body.

* * * * *